US006491948B1

(12) United States Patent
Buchholz et al.

(10) Patent No.: US 6,491,948 B1
(45) Date of Patent: Dec. 10, 2002

(54) COMPOSITION COMPRISING ISOQUERCETIN AND ASCORBIC ACID IN A SUSTAINED RELEASE FORM

(75) Inventors: Herwig A. Buchholz, Frankfurt (DE); Jerzy D. Meduski, Playa del Rey, CA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/525,457

(22) Filed: Mar. 15, 2000

Related U.S. Application Data

(60) Provisional application No. 60/124,863, filed on Mar. 16, 1999.

(51) Int. Cl.[7] ............................ A61K 9/22; A61K 9/20; A61K 9/52; A61K 9/54; A61K 9/14

(52) U.S. Cl. ........................ 424/468; 424/464; 424/457; 424/458; 424/484

(58) Field of Search ................................ 424/451, 457, 424/458, 484

(56) References Cited

U.S. PATENT DOCUMENTS 5,972,985 A * 10/1999 Thomas et al. ............. 514/200

FOREIGN PATENT DOCUMENTS

| | | |
|---|---|---|
| JP | 6-199690 | 3/1992 |
| JP | 06199690 A * | 7/1994 |

* cited by examiner

*Primary Examiner*—Thurman K. Page
*Assistant Examiner*—Rachel M. Bennett
(74) *Attorney, Agent, or Firm*—Millen, White, Zelano & Branigan, P.C.

(57) ABSTRACT

The present invention relates to novel, orally administered compositions comprising two redox systems: reduced ascorbic acid in a sustained release form and oxidized isoquercetin with an increased concentration of reduced vitamin C over a prolonged time in the brain. These compositions are useful as neuroprotective agents possessing preventive properties against memory dysfunctions.

24 Claims, No Drawings

COMPOSITION COMPRISING ISOQUERCETIN AND ASCORBIC ACID IN A SUSTAINED RELEASE FORM

This application claims the benefit of the filing date of U.S. Provisional Application Ser. No. 60/124,863 filed Mar. 16, 1999.

The present invention relates to novel compositions comprising ascorbic acid in a sustained release form and isoquercetin both with an increased bioavailability. These compositions are useful as food supplements possessing preventive properties against damage to human brain tissue due to oxidative stress. Specifically, these damages lead to memory loss, decline of cognitive abilities, premature aging.

BACKGROUND OF THE INVENTION

Study of biochemical events accompanying memory formation and memory regulation led us to an invention based on the novel concept of preventing an oxidative destabilization of DNAs, RNAs and proteins involved in neuronal memory processes [See Cohen, N. J., Eichenbaum, H. B. (1993) Memory, amnesia and the hippocampal system, Cambridge, Mass.: MIT Press; Olton, D. S. (1983) Memory functions and the hippocampus, in Seifert, W. (ed.) Neurobiology of the hippocampus, New York: Academic Press].

In vivo ascorbic acid (vitamin C) exists in three forms:

a) as an ascorbate in form of an ascorbate monoanion, b) as a free radical, called semidehydroascorbic acid which could be reversibly oxidized to dehydroascorbic acid or reversibly reduced to ascorbate monoanion, and c) as dehydroascorbic acid (oxidized form of semidehydroascorbic acid).

Only ascorbate possesses specific vitamin C activity as a cofactor for enzymes. Observed physiological activities of semidehydroascorbic acid and dehydroascorbic acid formed in vivo from ascorbate are considered to be based on their reversible reductions to ascorbates. See Buettner, G. R. (1993). The pecking order of free radicals and antioxidants: lipid peroxidation, alpha-tocopherol, and ascorbate, Arch. Biochem. Biophys. 300, 535–543; Dharival, K. R. et al. (1991), Semihydroascorbic acid as an intermediate in norepinephrine biosynthesis in chromaffin granules, J. Biol. Chem. 266, 12908–12914; and Welch, R. W. et al. (1995), Accumulation of vitamin C (ascorbate) and its oxidized metabolite dehydroascorbic acid occurs by separate mechanisms, J. Biol. Chem. 270, 12584–12592.

The second form of ascorbic acid, semidehydroascorbic acid (ascorbate free radical) participates in univalent redox systems that is in the antioxidant defense activity. See Bors, W. et al. (1995), Interaction of Flavonoids with Ascorbate and Determination of their Univalent Redox Potentials: a Pulse Radiolysis Study, Free Radical Biology and Medicine, vol. 19, No. 1, 45–52. This means semidehydroascorbic acid participates most likely in free radical scavenging activities. According to the article Gordon, M. H. (1996), Dietary Antioxidants in Disease Prevention, Natural Product Reports, pp. 265–273, "ascorbate appears to be the most important non-protein antioxidant in plasma" p. 270. Ascorbic acid is not able to cross blood-brain barrier. In contrast, dehydroascorbic acid readily enters the brain. See Agus, D. B. et al. (1997), Vitamin C crosses the blood-brain barrier in the oxidized form through the glucose transporters, J. Clin. Invest., 100 (11) 2842–2848. After entering the brain dehydroascorbic acid is reduced and retained as ascorbic acid.

Structures of body tissues are susceptible to damages caused by the oxidative stress, e.g. by the accumulation of reactive oxygen species during aging, chronic environmental stress, inflammations or general metabolic dysfunctions. The role of free radicals and reactive oxygen species in aetiology of a variety of human diseases including brain dysfunctions is well established. See: Gordon, (1996) supra. Uncontrolled generation of free radicals, especially chronic exposure to reactive oxygen species leads to chronic intracellular damage, to oxidative stress and premature aging. Oxidative stress and the decreased ability of the body to maintain the regulation of intermediary redox systems play a crucial role in age-related brain function decline, memory loss, and a number of neurodegenerative disorders. The formation and accumulation of free radicals lead to excessive lipid peroxidation, amyloid deposition, degeneration of brain and peripheral neurons, and cell death. See Floyd, R. A., Carney, J. M. (1996), Free radical damage to protein and DNA: mechanisms involved and relevant observations on brain underoing oxidative stress, Ann. Neurol., 32, 522–527.

Cells of the human body including brain cells possess metabolic antioxidant defenses which are supported by dietary antioxidants. The early observations of the antioxidant defense metabolic processes involved vitamin C and flavonoids. See Bezssonoff, N. (1926), L'effet antiscorbutique est-il du a deux substances differentes?, C.r. Acad. Sci., Paris 183, 1309–1310; Bull. Soc. Chim. Biol. (1927) 9, 568–579; Bentsath, A., Szent-Gyorgyi, A. et al. (1936), Vitamin natur of flavones, Nature (London) 138, 798; Bentsath, A., Szent-Gyorgyi, A. et al. (1937), Vitamin P, Nature (London) 139, 326–327; and Blanc, B. and Von der Muehl, M. (1967), Interaction d'une flavonoide et vitamine C; son influence sur le poids du cobaye et le contenu en vitamine C de ses organs, Int. Z. VitaminForsch., 37,156–169.

Oxidation of the ascorbate in the human body by xenobiotics often leads to the accumulation of semidehydroascorbic acid or dehydroascorbic acid in organs where these forms interfere with the regular metabolism. Vitamin C is believed to play a critical role in the central nervous system. See Englard, S. and Seifter, S. (1986). The biochemical functions of ascorbic acid, Ann. Rev. Nutr. 6, 365–406; Padh, H. (1990), Cellular function of ascorbic acid, Biochem. Cell. Biol., 68, 1166–1173. It is involved in catecholamine biosysnthesis (as a cofactor of dopamine-beta-hydroxylase). It also acts as free radical scavenger inhibiting the peroxidation of membrane phospholipids. The decrease of the concentration of ascorbate in brain tissue may lead to serious metabolic dysfunctions.

The concentration of vitamin C in brain is higher than in other organs. See Kaufman, S. (1966), Coenzymes and hydroxylases: ascorbate and dopamine-beta-hydroxylase: tetrahydropteridines and phenylalanine and tyrosine hydroxylases, Pharmacol. Rev., 18, 61–69. Particularly, it is 10 times higher than in blood serum. See Honig, D. (1975), Distribution of ascorbic acid, metabolites and analogues in man and animals, Ann. N.Y. Aca. Sci., 258, 103–118. An active transport mechanism exists for carrying ascorbic acid from blood to brain. It has been found that dehydroascorbic acid is transported through facilitative glucose transporters. See Vera, J. C. et al. (1993), Mammalian facilitative hexose transporters mediate the transport of dehydroascorbic acid, Nature, 364, 79–82. The concentration of vitamin C in brain may be increased by increasing the blood concentration of dehydroascorbic acid.

The possibilities to protect ascorbic acid in vivo were based on very early observations of Szent-Gyorgyi group mentioned above that the ascorbic acid activity in humans and guinea pigs is intensified by the great group of "vegetable dyes, the flavons or flavonols". It has been known that flavonoids are contributing to the maintenance of the concentration of the administered ascorbate in adrenals, kidneys, spleen, and the liver of the organisms investigated and improve the antiscorbutic effect of the dosages of ascorbate used. See Cotereau, H. et al. (1948), Influence of vitamin P (C2) Upon the amount of ascorbic acid in the organs of the guinea pig, Nature, 161, 557–558; Crampton, E. W. et al. (1950), A qualitative estimation of the effect of rutin on the biological potency of vitamin C, J. Nutr., 41, 487–498; Blanc, B. and Von der Muehl, M., supra; and Zloch, Z. (1973), Einfluss von Bioflavonoiden auf den Vitamin C-Wert kristallliner Deydroascorbinsaure, Int. J. Vit. Nutr. Res. 43, 378–386.

The mechanism of this effect, called "the vitamin C-economizing function" of some flavonoids ("facteur d'economie de L'acide ascorbique" of Bezssonoff, 1926 and 1927, supra) has been recognized in many laboratories. For example, it was found that, among flavonoids tested, flavonols have the strongest ability to inhibit ascorbic acid oxidation in near neutral solutions (pH 5–7). See Harper, K. A. et al., (1969) Phenolic compounds of black currant juice and their protective effect on ascorbic acid. III Mechanism of ascorbic acid oxidation and its inhibition by flavonoids, J. Food Tech., 4, 255–267. Harper et al. (1.c.) also pointed out that the presence of free hydroxyl groups at carbon atoms 3, 7, 3', and 4' in a flavonol molecule improves the antioxidative effect of the flavonol molecule, this means, it inhibits ascorbate oxidation more effectively.

But there was neither an effective method nor a useful orally applicable formulation leading to an increased level over a polonged period of active ascorbate in human brain tissue.

Accordingly, there was a need for a composition useful for the protection of the orally administered ascorbic acid and enhancement of this vitamin activity in the brain.

Now it has been found that isoquercetin effectively inhibits ascorbate oxidation. The maintenance of the reduced form of ascorbic acid by isoquercetin maintains ascorbic acid level in body tissues and fluids. The increased effectivity of ascorbate protection may be caused by the fact that isoquercetin contains a glucose molecule. This glucose molecule seems to be the reason why isoquercetin is able to use the sodium-dependent glucose transport pathway of the intestinal brush-border membrane in its absorption process. See Gee, J. M. et al. (1998), Quercetin glucosides interact with the intestinal glucose transport pathway, Free Radical Biology and Medicine, 25, (1), 19–25. Isoquercetin is also able to use similar glucose transporters used by the oxidized ascorbic acid (that is by dehydroascorbic acid) crossing the blood-brain barrier. See Agus supra.

It was found that if isoquercetin is given one hour before ascorbate, isoquercetin enters the brain and reduces dehydroascorbate which represents dietary ascorbic acid oxidized during the passage of blood-brain barrier.

This means, there is an interaction of two redox systems leading to the synergistic effect between isoquercetin and ascorbate in human brain tissue leading to higher effectivities of both, ascorbate and isoquercetin.

For isoquercetin biological activities are as follows:

it inhibits the biosynthesis and release of prostaglandin-like substances, (Chanh, P. H. et al. (1986) Comparative effects of total flavonoids extracted from Ribes nigrum leaves, rutin and isoquercitrin on biosynthesis and release of postaglandins in the ex vivo rabbit heart, Prostaglandins 1. Med., 22, 295–300);

it produces dose-dependent protection against oxidative DNA damage, (Noroozi, M. et al. (1998) Effects of flavonoids and vitamin C on oxidative DNA damage to human lymphocytes, American Journal for Clinical Nutrition, 67, 1210–1218);

it possesses preventive properties against damages of vascular tissues in brain and other organs.

Now it has been found that an orally administered combination of ascorbic acid in a sustained release form and isoquercetin conveys in vivo higher protection, longer maintenance of biological activity, higher concentration in brain tissue and higher biological efficiency to vitamin C in human body. This combination also provides the properties of higher protection, longer maintenance of biological activity, higher concentration in brain tissue and higher biological efficiency in human body to isoquercetin.

The object of the present invention is therefore an orally applicable composition comprising ascorbic acid, ascorbate or a derivative of ascorbic acid or ascorbate in a sustained release form and quercetin-3-O-glucoside (isoquercetin).

Preferred compositions comprise the ascorbic acid or a derivative thereof and isoquercetin in a molar ratio of ascorbate to flavonoid in the range of 2:1 to 1:2, preferably in the molar ratio of 1:1.

Useful compositions may contain in a daily dose 100–1000 mg of an active amount of ascorbic acid, or a mixture of ascorbic acid and dehydroascorbic acid, or physiologically active ascorbate in form of its mineral or organic cation salts. The compositions according to the present invention may be prepared in form of tablets, capsules or syrups. These application forms may also contain further active ingredients in useful amounts.

The compositions of the present invention preferably are useful as food supplements, but they may also be administered in a pharmaceutical treatment.

The present invention makes available a) a method of maintaining long biological activity and high concentration of reduced form of ascorbate and oxidized form of isoquercetin in human brain tissue, b) a method of protection against oxidative damages of human brain tissue that affect the memory, c) a method of prevention of damages of vascular tissues, in the central nervous system and other organs of the body, that contribute to premature aging, d) a method of supporting pharmacological treatments of diseases and dysfunctions caused by oxidative damages in the brain tissue, by orally administration of a composition described above and/or related or suggested modifications of this composition. Generally speaking, compositions that are applicable comprise at least one substance in a sustained release form selected from ascorbic acid or ascorbate or any other form of this vitamin that would in vivo yield ascorbate, or semidehydroascorbic acid, or dehydroascorbic acid, and additionally isoquercetin. The decision which further ingredients should be components of a composition useful in one of the above mentioned methods depends on the special indication. Usually, if the composition is administered as a way of protection or prevention useful further ingredients may be further vitamins, salts of Mg, Ca, K, Fe and trace elements in known amounts as used in food supplements. Compositions useful in method of supporting pharmacological treatments may differ from them.

The superiority of isoquercetin and ascorbate (in time release form) used in combination for the protection of human brain cells from the oxidative stress is based on several properties of isoquercetin and of ascorbate. First, on the quick intestinal absorption of orally administered isoquercetin. Secondly, on the rapid and simple passage of isoquercetin and dehydroascorbic acid through blood-brain barrier. Thirdly, on the specificity of interaction of isoquercetin with ascorbate. Particularly, ascorbate maintains isoquercetin in its active oxidized state and isoquercetin maintains ascorbate in its enzymatically active reduced state. After passing blood-brain barrier the dehydroascorbic acid becomes re-reduced with the help of isoquercetin and is able to participate in enzymatic reactions in the brain.

On the basis of our research on the bioavailability and on redox properties of isoquercetin and ascorbate it has been found that orally administered mixtures of isoquercetin and ascorbate in a sustained release form are most effective in protecting the brain tissue from chronic intracellular oxidative damages; in this way preventing ameliorating or restoring functional damages of brain neurons.

The uptake of isoquercetin into the human brain is caused by the sodium-dependent glucose transport system. This type of transport occurring in most animal species (Coady, M. J. et al. (1990), Sequence Homologies between Intestinal and renal N(+)/glucose cotransporters, Am. J. Physiol. 259, 605–610) is active during the uptake of pyranosides as for example described by Hediger for methyl alpha-D-glucopyranoside (Hediger, M. A. et al. (1987), Expression and Cloning and CDNA Sequencing of the Na(+)/glucose cotransporter, Nature, 330, 379–381). The sodium-dependent glucose transport system in mammals was studied in many laboratories. The susceptibility of isoquercetin to be transported using the Na(+)-D-glucose cotransport is determined by the manner in which a non-glucose moiety is linked to glucose. More information about this is given in a review of Olson, A. L. and Pessin, J. E. (1996), Structure, function and regulation of the mammalian facultative glucose transporter gene family, Annual Rev. of Nutrition, Vol 16, 235–256. The uptake of ascorbate by human brain tissue is caused by a sodium dependent glucose transport system. Interactions between glucose and ascorbate transport activity have been demonstrated in many tissues and cells. See Rumsey, S. C. and Levine, M. (1998), Absorption, Transport and disposition of ascorbic acid in humans, Nutritional Biochem. 9, 116–130.

Pharmacokinetic studies with isoquercetin support the present invention as they show excellent absorption rate and bioavailability of isoquercetin. It is absorbed better than rutin and quercetin (Hollman, P. (1997), Determinants of the absorption of the dietary flavonoid quercetin in man, Proefschrift, Universiteit Nijmegen). Absorbed isoquercetin interacts with ascorbate keeping it in the reduced state and, at the same time, is being protected by ascorbate by being kept in the oxidized state (Yamasaki, H. et al. (1997), Flavanoid-peroxidase reaction as a detoxification mechanism of plant cells against $H_2O_2$).

Therefore, a highly efficient dietary antioxidant composition is prepared using reduced ascorbic acid in a sustained release form and oxidized isoquercetin. The advantageous properties of this composition are induced by the synergistic effect of oxidized isoquercetin protecting the activity of the orally administered reduced ascorbic acid by maintaining its (ascorbic acid) enzymatically active reduced form. At the same time ascorbic acid maintains isoquercetin in its active oxidized state.

Subject of this invention is that in humans the oral administration of a combination of isoquercetin and ascorbic acid in time release form conveys efficient protection of the brain against oxidative damages, due to long maintenance of biological activity and of the concentration of both ascorbate and isoquercetin in the brain tissue.

According to the invention ascorbic acid or one of its derivative is used in a sustained or time release form. The sustained release forms can involve a wide variety of physical modifications of ascorbic acid. Such modifications are generally well known to those skilled in the art, and do not in themselves form part of the present invention.

For example, the solid ascorbic acid may have a coating which is not readily water-soluble but which is slowly attacked and removed by water, or through which water can slowly permeate.

Thus, for example, L-ascorbic acid powder, which passes through a 200-mesh screen, is spray-coated with a solution of a binder under continuously fluidizing conditions. See Kitamori et al., U.S. Pat. No. 4,036,948. As the binder, there may be mentioned water-soluble binders such as pregelatinized starch (e.g., pregelatinized corn starch, pregelatinized white potato starch), pregelatinized modified starch (see Code of Federal Regulation (U.S.A.) Para. 121,1031, a,b,c, d,e,f,g, and h), water-soluble celluloses (e.g. hydroxypropylcellulose, hydroxymethyl-cellulose, hydroxypropylmethylcellulose, carboxymethyl-cellulose), polyvinylpyrrolidone, polyvinyl alcohol, dextrin, gum arabicum and gelatin, organic solvent-soluble binders, such as cellulose derivatives (e.g., cellulose acetate phthalate, hydroxypropylmethyl-cellulose phthalate, ethylcellulose).

Alternatively, the acid can be distributed throughout a support matrix which is not readily water soluble but which, like the above-mentioned coating, is slowly attacked and removed by water or can be permeated by water slowly.

Spray-dried ascorbic acid also has been found to have sustained release properties, and the present invention encompasses this form of acid. Preferably, the composition of the invention is provided in unit dosage form, and each unit dose may contain from 100 mg to 1000 mg of sustained release ascorbic acid.

One particular form of sustained release ascorbic acid comprises particles of ascorbic acid coated with different thicknesses of hydrophobic coating materials such as beeswax, glycerylmonostearate, stearic acid or cetostearyl alcohol. A silicon coating can also be used. A mixture of such particles having coatings of different thicknesses provides a timed release of ascorbic acid when swallowed. Such a mixture of particles is conveniently carried in a conventional gelatine capsule for oral administration. In one example of a composition of the invention, isoquercetin would be included together with the mixed coated ascorbic acid particles in a gelatine capsule.

Another particular form of sustained release ascorbic acid may be prepared by granulation of the powdered ascorbic acid, together with various hydrophobic excipients to produce a hydrophobic matrix with the ascorbic acid distributed throughout. The matrix may contain from 50 to 99% by weight of ascorbic acid, preferably from 75 to 99%. When swallowed, gastric fluid penetrates the matrix and, over a prolonged period, the ascorbate is leached out. The timing of the release is controlled by varying the pore size of the matrix. Suitable hydrophobic matrices are provided by fats and waxes or synthetic or natural resins such as polyvinyl chloride, polyethylene, vinyl acetate/vinyl chloride copolymer, sandarac resin or copal resin. The tiny granule matrices produced by these methods can be compressed into tablets together with conventional tabletting excipients or can be carried in conventional gelatine capsules.

Yet another form of sustained release ascorbic acid is prepared by microencapsulation of particles of ascorbic acid in membranes which act as microdialysis cells, i.e. gastric fluid permeates the microcapsule walls, swells the microcapsule and the ascorbate dialyses out. See, for example, Tsuei, A. C. et al., U.S. Pat. No. 5,589,194. One commercially available sustained release ascorbic acid of this kind consists of microcapsules having membranes of acacia gum/gelatine/ethyl alcohol. This commercial product is available from Eurand Limited (France) under the trade name "Diffucaps". Again, as an example of a composition of the invention embodying this kind of sustained release ascorbic acid, the microcapsules might be carried, together with the isoquercetin in a conventional gelatine capsule. Alternatively the microcapsules could be also tabletted.

A further sustained release form of ascorbic acid is enteric coated ascorbic acid. As such formulations release ascorbic acid only in the alkaline conditions of the intestine, release is sustained by prolonged gastric emptying or, when used in overdose, by the effect of acid-release buffers that decrease pH of the intestinal contents to less basic pH, slowing further release. Enteric coatings are well known in the art. Suitable coatings include cellulose acetate phthalate coatings (e.g. Eudragit).

Thus, a further object of this invention is that ascorbic acid is in the form of solid ascorbic acid having a water resistant or water permeable coating, or of spray dried ascorbic acid, or of a hydrophobic matrix having ascorbic acid particles distributed throughout, or of enteric coated ascorbic acid or microencapsulated ascorbic acid.

Regarding this invention for a single dosage form in which both a quick- and slow-release ingredients are co-administered a preferred approach would be the "microencapsule method". For the different methods of microencapsulation see for instance U.S. Pat. No. 4,292,298 (1981) or U.S. Pat. No. 5,589,194 (1996).

The advantage of administering a time-release form of ascorbate is based on the following: isoquercetin enters the brain first reducing some of the later arriving dehydroascorbate—being also there in a certain concentration—which presents dietary ascorbic acid oxidized to dehydroascorbic acid during passage of blood-brain barrier. Then more slowly administered ascorbic acid continues to be reduced in the brain by isoquercetin "waiting" ready to reduce it to obtain the active ascorbate. The concentration of vitamin C in the brain is increased over a long period of time and therefore, the sustained release form prolongs the whole process and thus prolongs the effect of protection against any damage to brain tissue.

Isoquercetin and the sustained release ascorbic acid may be administered together or consecutively. Consecutively means that first isoquercetin is administerd and after a period of time, preferably about after one hour, ascorbic acid is administered. In this case it is also possible—and even preferred—to use the normal ascorbic acid or its derivative and not the time release form.

Therefore, another object of the present invention is that the two active substances of the composition according to this invention are administered sequentially that means that at first isoquercetin is administered and after a period of time ascorbic acid, ascorbate or its derivative is administered, preferably the ascorbic acid being not in a sustained release form.

In another aspect of the present invention there is provided a treatment pack comprising an oral dosage unit comprising isoquercetin and an oral dosage unit comprising ascorbic acid or a sustained release form thereof, these two oral dosage units being retained in said pack in association with one another, e.g. by blister packing the two dosage units in the same blister.

The invention of this application includes compositions containing the above mentioned ingredients useful for the prevention and treatment of any damage to human brain tissue due to oxidative stress. Specifically, these damages lead to memory loss, decline of cognitive abilities, premature aging.

The entire disclosure of all applications, patents and publications, cited above and below are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A composition for oral administration, comprising ascorbic acid, ascorbate or a derivative of ascorbic acid or ascorbate in a sustained release form and quercetin-3-O-glucoside (isoquercetin) in a non-sustained release form.

2. A composition according to claim 1 comprising isoquercetin in combination with a sustained release form of ascorbic acid or a mixture of ascorbic acid and dehydroascorbic acid, or a physiologically active ascorbate in the form of a mineral or organic salt.

3. A composition according to claim 1 comprising a combination of isoquercetin and a sustained release form of ascorbic acid, dehydroascorbic acid, or a mineral or organic salt thereof.

4. A composition according to claim 1 in which the sustained release ascorbic acid is in the form of solid ascorbic acid having a water resistant or water permeable coating, or spray dried ascorbic acid, or a hydrophobic matrix having ascorbic acid particles distributed throughout, or enteric coated ascorbic acid or microencapsulated ascorbic acid.

5. A composition according to claim 1 which additionally comprises other vitamins.

6. A composition according to claim 1 which additionally comprises suitable salts of Mg, Ca, K and Fe.

7. A composition according to claim 1 which additionally comprises trace elements.

8. A composition according to claim 1 comprising ascorbic acid or ascorbate in a sustained release form and isoquercetin in a molar ratio in the range of 2:1 to 1:2.

9. A composition according to claim 1 comprising ascorbic acid or ascorbate in a sustained release form and isoquercetin in a molar ratio of about 1:1.

10. A composition according to claim 1 in the form of a dosage unit, comprising 100–1000 mg ascorbic acid or ascorbate.

11. A method of supplementing nutrition provided by food comprising administering the composition of claim 1 as a food supplement.

12. A method of stabilizing the biological activity of intracellular components in and stabilizing high concentrations of a reduced form of ascorbate and an oxidized form of isoquercetin in, human brain tissue, comprising orally administering to a patient in need thereof a composition according to claim 1, wherein said biological activity is the regulation of intermediary redox systems, the proper regulation of lipid peroxidation and/or amyloid deposition, and/or the maintenance of brain and peripheral neurons against degeneration and/or cell death.

13. A method of protection against oxidative damage to brain tissue, comprising orally administering to a patient in need thereof a composition according to claim 1.

14. A method of administering two or more pharmacological agent to treat a disease or dysfunction caused by oxidative damage which comprises orally administering to a patient in need thereof a composition according to claim 1.

15. A pharmaceutical composition comprising a pharmaceutically active ingredient, a pharmaceutically acceptable carrier and a composition according to claim 1.

16. A method of administering isoquercetin and ascorbic acid, ascorbate or a derivative of ascorbic acid or ascorbate sequentially to a patient in need thereof, comprising administering the isoquercetin, and, then, thereafter, ascorbic acid, ascorbate or a ascorbic acid or ascorbate at an interval between administrations whereby the isoquercetin and ascorbic acid, ascorbate or a derivative of ascorbic acid or ascorbate are simultaneously bioavailable or at an interval between administrations of one hour.

17. The method according to claim 16, wherein the ascorbic acid, ascorbate or the derivative of ascorbic acid or ascorbate is not in a sustained release form.

18. A kit for administering isoquercetin and ascorbic acid, ascorbate or a derivative of ascorbic acid or ascorbate, comprising an oral dosage unit comprising isoquercetin and an oral dosage unit comprising ascorbic acid, ascorbate or a derivative of ascorbic acid or ascorbate.

19. The kit according to claim 18, wherein the two oral dosage units are retained in the treatment pack in association with one another.

20. The kit according to claim 19, wherein the two oral dosage units are in the same blister of a blister pack.

21. A method of treating a memory dysfunction, comprising orally administering a composition according to claim 1 to a patient in need thereof.

22. A method of claim 12, wherein the patient is human.

23. A composition for oral administration, comprising ascorbic acid, ascorbate, or a physiologically active mineral or organic salt thereof, in a sustained release form and quercitin-3-O-glucoside (isoquercetin) in a non-sustained release form.

24. A method of treating progressive loss of memory, comprising orally administering to a patient in need thereof a composition according to claim 1.

* * * * *

UNITED STATES PATENT AND TRADEMARK OFFICE

CERTIFICATE OF CORRECTION

PATENT NO. : 6,491,948 B1
DATED : December 10, 2002
INVENTOR(S) : Herwig A. Buchholz et al.

It is certified that error appears in the above-identified patent and that said Letters Patent is hereby corrected as shown below:

Column 8,
Lines 17 and 22, reads "claim 1 comprising" should read -- claim 1, comprising --
Line 26, reads ""claim 1 in which" should read -- claim 1, in which --
Lines 33, 35 and 37, reads "claim 1 which additionally" should read -- claim 1, which additionally --
Lines 39 and 42, reads "claim 1 comprising" should read -- claim 1, comprising --
Line 45, reads "claim 1 in the form" should read -- claim 1, in the form --
Line 52, reads "components in and" should read -- components in, and --
Line 65, reads "agent to" should read -- agents to --

Column 9,
Line 8, reads "ascorbate or a ascorbic acid" should read -- ascorbate or a derivative of ascorbic acid --

Column 10,
Line 14, reads "quercitin-3-0-glucoside" should read -- quercetin-3-0-glucoside --

Signed and Sealed this

Seventh Day of October, 2003

JAMES E. ROGAN
*Director of the United States Patent and Trademark Office*